(12) United States Patent
Copelan

(10) Patent No.: US 6,331,278 B1
(45) Date of Patent: Dec. 18, 2001

(54) SELF-CONTAINED DOUBLE HANDHOLD FOR PREVENTING FALSE URINE SPECIMENS

(76) Inventor: Herbert W. Copelan, 875 E. Camino Real, Apt. 14-E, Boca Raton, FL (US) 33432

( * ) Notice: Subject to any disclaimer, the term of this patent is extended or adjusted under 35 U.S.C. 154(b) by 0 days.

(21) Appl. No.: 09/804,314

(22) Filed: Mar. 13, 2001

(51) Int. Cl.$^7$ ............................................. B01L 3/00
(52) U.S. Cl. ......................... 422/102; 422/61; 422/939; 436/174; 436/180; 600/573
(58) Field of Search .................. 422/61, 99, 102, 422/939; 436/174, 180, 901; 600/573, 574; 206/807

(56) References Cited

U.S. PATENT DOCUMENTS

| | | | |
|---|---|---|---|
| 4,769,215 | * 9/1988 | Ehrenkranz | 422/58 |
| 5,039,616 | * 8/1991 | Copelan | 436/56 |
| 5,069,878 | * 12/1991 | Ehrenkranz | 422/61 |
| 5,133,935 | * 7/1992 | Copelan | 422/61 |
| 5,179,027 | * 1/1993 | Fisher | 436/56 |
| 5,223,221 | 6/1993 | Copelan . | |
| 5,352,410 | * 10/1994 | Hansen et al. | 422/58 |
| 5,603,903 | 2/1997 | Copelan . | |

* cited by examiner

*Primary Examiner*—Maureen M. Wallenhorst

(57) ABSTRACT

A self-contained double handhold that is a complete device for preventing a subject's hands from putting a false specimen into a container. Previous hand-restricting apparatus was too cumbersome and unwieldy to be used. The present device is practical. It is about the size and shape of a tall water tumbler. The double handhold consists of two independently operable, hollow units, each of which restricts one hand. The units telescope part way together to secure the container inside and must be separated to allow access to it. Locking the units together requires only one latch, but the device uses two latches, each controlled by a different one of the two units. Thus, both hands must be engaged at the same time to open the two latches, separate the units, expose the container, and reassemble the two units. The container is housed in the lumen of one unit, which is held naturally in the hand. When the units are separated, access to the container is almost as direct and convenient as with a free container. The subject is not encumbered. If a hand does not maintain proper engagement, its latch closes automatically. The closed latch bolt then blocks assembly of the units, and the subject cannot reopen the latch. Thus, a breach of procedure is evident if the subject does not keep both hands restricted while the container is accessible.

10 Claims, 5 Drawing Sheets

SELF-CONTAINED DOUBLE HANDHOLD FOR PREVENTING FALSE URINE SPECIMENS

FIELD OF INVENTION

This invention relates to collecting urine specimens for drug-abuse testing, specifically to apparatus that restricts a subject's hands to prevent cheating.

DESCRIPTION OF PRIOR ART

To prevent a false urine specimen, it has been necessary for an attendant to watch the subject urinate into a container. To avoid this violation of personal privacy, portable, two-hand-restricting container holders were proposed. These have not been practical because they were unwieldy, as can be seen from U.S. Pat. Nos. 5,223,221 (1993) and 5,603,903 (1997), both to Copelan.

To simultaneously restrict both hands from access to the container, the devices used two handles that were operated together in a combined mechanism. Necessarily, the handles were mounted as a pair on a single, crossbar-like part of the various devices. Both hands were restricted, but the devices were not acceptable. Their bulk was cumbersome. Holding on to the two handles was awkward. Voiding was further complicated by the container's required location, either attached inconveniently to the crossbar or in a separate section of apparatus. The contrivances were particularly impractical in the confined space of a lavatory.

ADVANTAGES OF PRESENT INVENTION

The present device is a practical means for restricting the hands when collecting a urine specimen, Several features are novel for a hand-restricting apparatus:

1. The entire device is a double handhold, a cylinder less than 25 cm. (10 inches) long. It is completely self-contained. No additional elements are necessary or desirable.
2. The double handhold consists of two hollow, single-hand units assembled together to enclose a container. The subject must have one hand engaged on each of the units to separate them, expose the container, and reassemble the device.
3. Each unit effectively restricts a hand. It is not necessary to yoke the hands together on a cumbersome crossbar or at a distance from the container.
4. The units are partly telescoped together to form the double handhold. This makes the joint secure and the device conveniently small.
5. One latch is sufficient to lock the device, but it has two. Thus, each unit can use an independent latch mechanism so that the units can be separated.
6. Separating the units frees the arms, and the container is easily positioned for voiding.
7. The container rests in one unit, which is held in the hand. Access is natural.

The assembled double handhold is about the size and shape of a tall water tumbler. It is convenient even in a small lavatory. It is not an encumbrance when preparing to void. After the units are separated, the subject's arms can move independently. Posture and balance are not disturbed. Voiding is almost as simple as with a container by itself.

DRAWING FIGURES

Closely related figures have the same number but different alphabetical suffixes.

FIGS. 1A, 1B, and 1C are right-side views of three cylinders: the assembled double handhold, its lower unit, and the lower half of the upper unit.

FIGS. 2A and 28 are midline cross-sections of each unit, viewed from the right side.

Figure 1A:
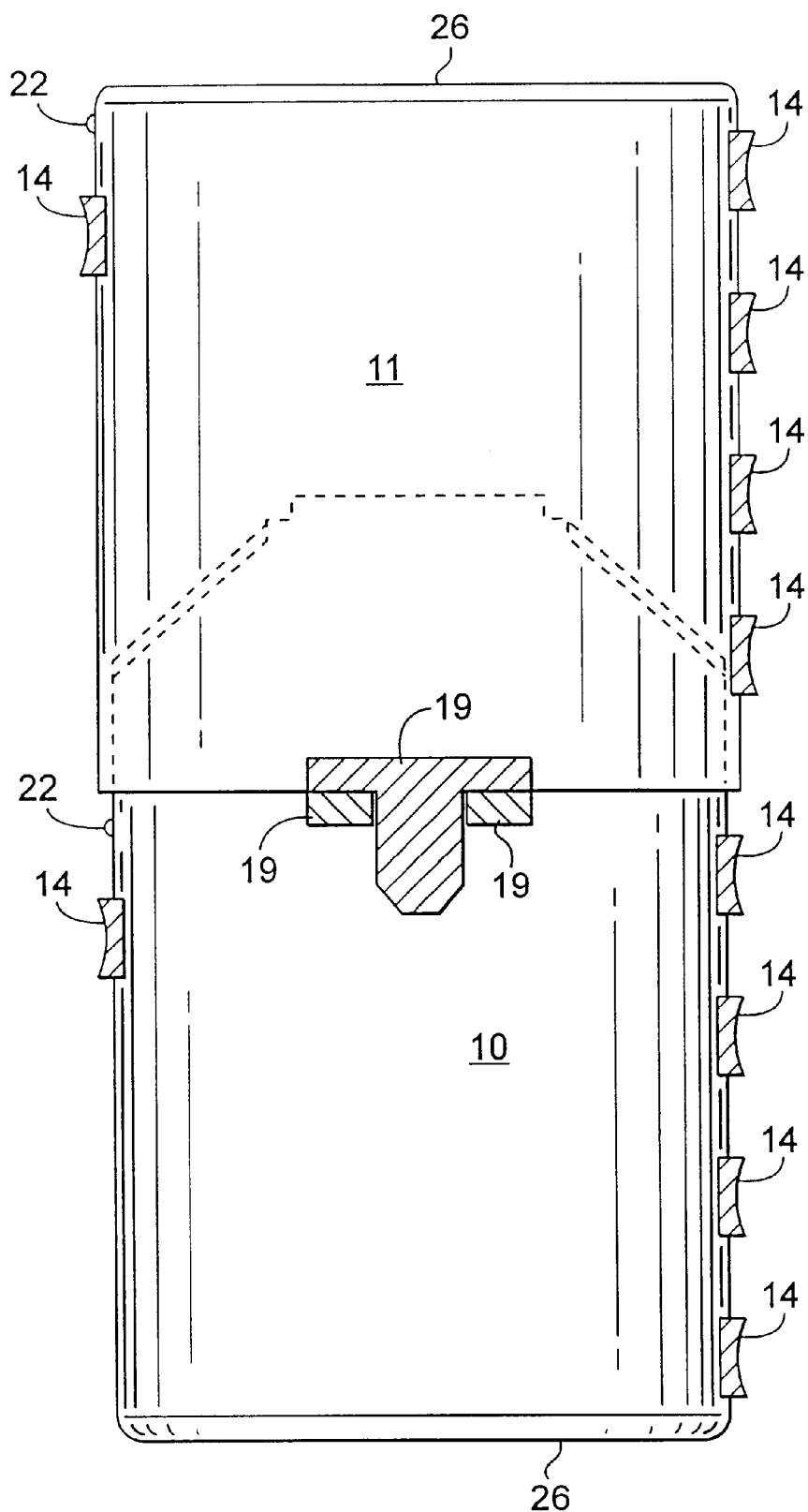

FIGS. 6A, 6B, 6C, and 6D shows a switch

REFERENCE NUMERALS IN DRAWINGS 10 lower unit
11 upper unit
12 container
13 disposable element
14 actuator
16 latch bolt
17 coupler
18 aperture
19 guide
20 motor
21 battery
22 breach signal
23 shelving
24 switch terminals
25 switch connector
26 service door
27 coupler port

DESCRIPTION OF FIGS. 1 to 6

Figure 1C:
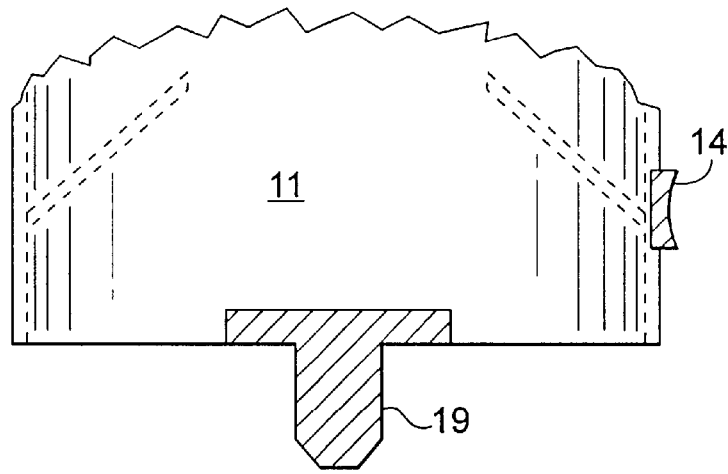
Figure 1B:
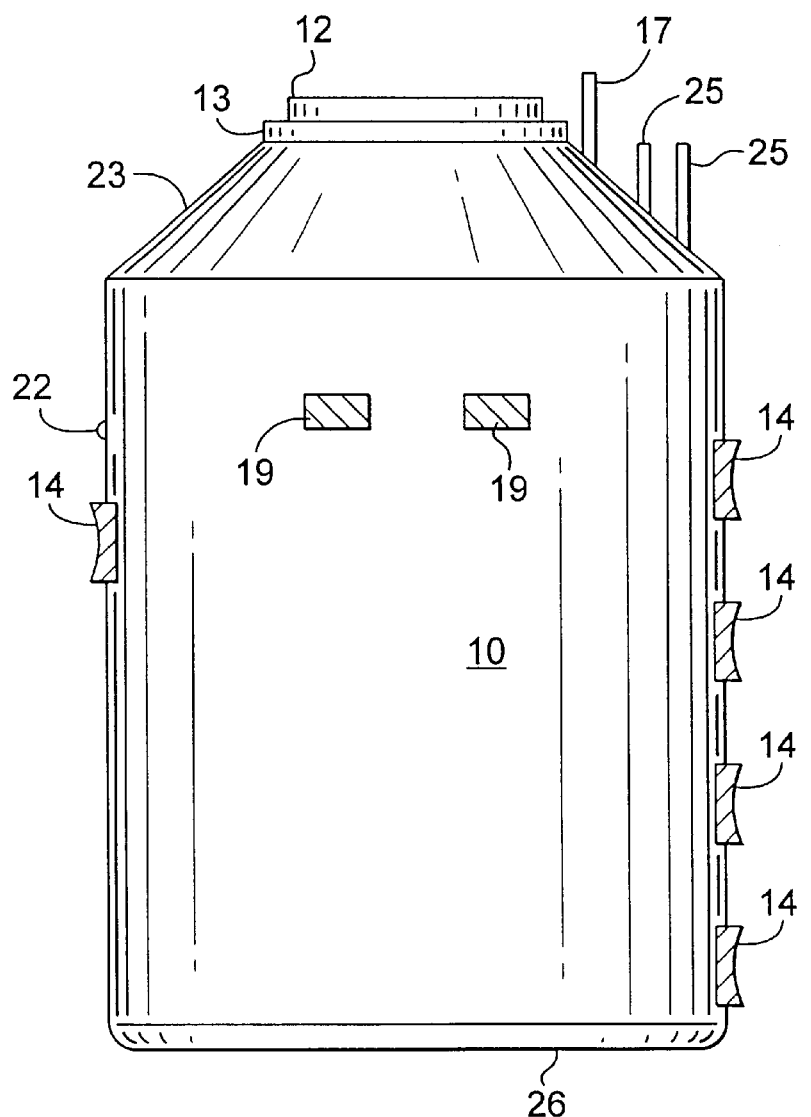

FIG. 1A shows the preferred embodiment with the two units assembled together. The bottom of upper unit 11 telescopes over the top of lower unit 10 to cover its open end. FIG. 1B shows diagonal shelving 23 that fits unit 10 for assembly. Each unit has five actuators 14, one for each digit. In FIG. 1B, a switch connector 25 is visible on shelving 23 of unit 10. The tops of container 12 and disposable element 13 are seen. FIG. 1C shows the lower, telescoping part of unit 11 and the projecting part of guide 19.

Figure 2B:
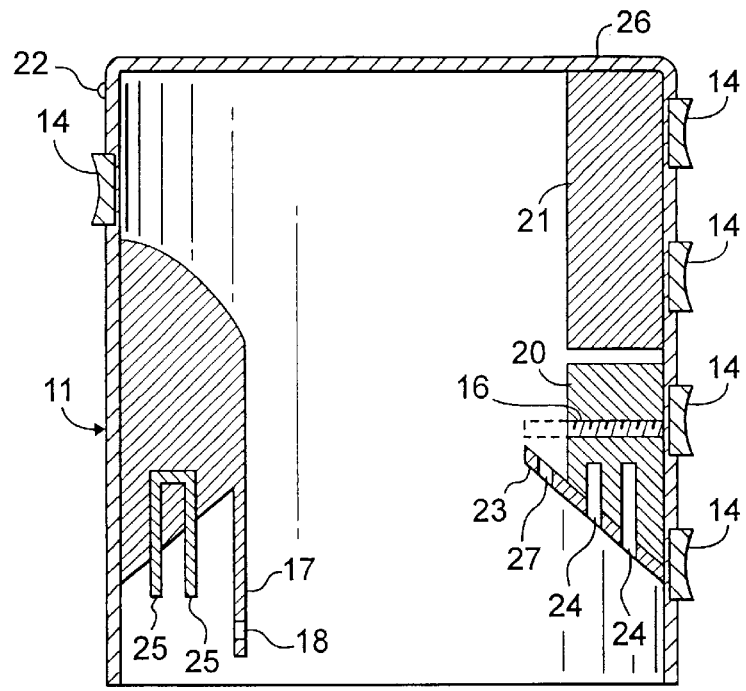
Figure 2A:
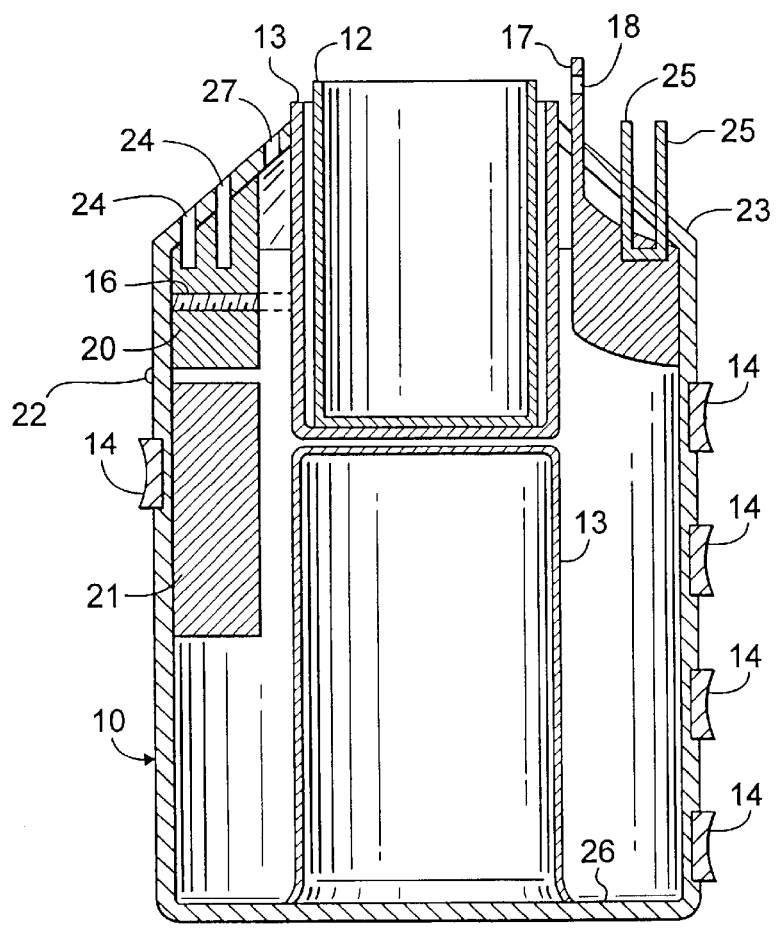

FIG. 2A shows container 12 resting in disposable element 13 in the lumen of lower unit 10. Two disposable elements 13 are used, one inverted as a base for the other. FIGS. 2A and B illustrate the locations of each latch bolt 16, coupler 17, terminals 24, switch connectors 25, motor 20, and battery 21. Each unit has shelving 23 and a service door 26.

Figure 3A:
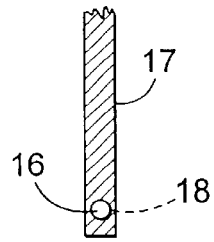
FIGS. 3A, 3B, 3C and 3D shows a latch bolt and its coupler.
Figure 3B:
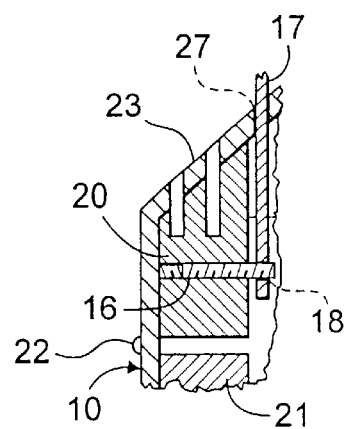
Figure 3C:
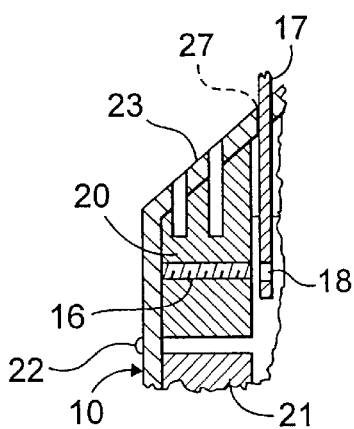
Figure 3D:
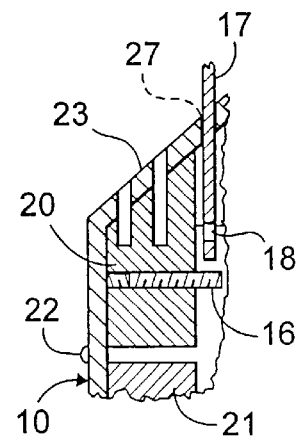

FIG. 3A shows a coupler 17 with aperture 18 for latch bolt 16. FIG. 3B shows latch bolt 16 closed. FIG. 3C shows bolt 16 in position to close. FIG. 3D shows coupler 17 blocked by premature closure of bolt 16.

Figure 4A:
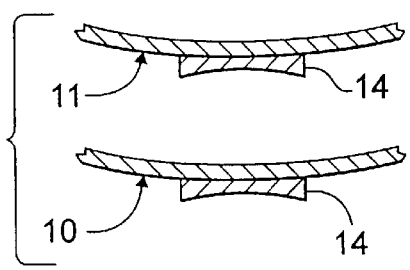
FIGS. 4A and 4B shows an actuator
Figure 4B:
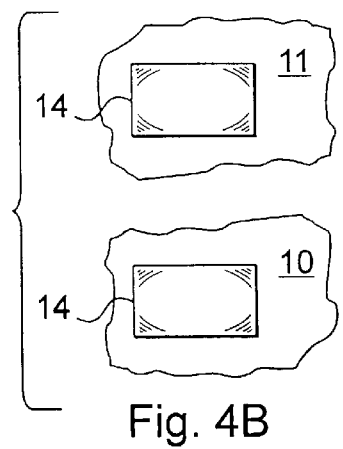

FIGS. 4A and 4B shows top and frontal views of actuator 14.

Figure 5A:
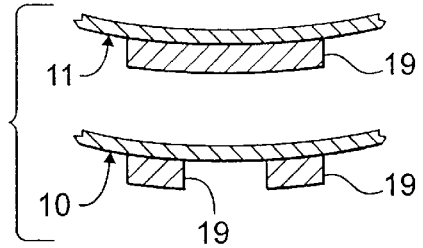
FIGS. 5A, 5B and 5C shows an assembly guide
Figure 5B:
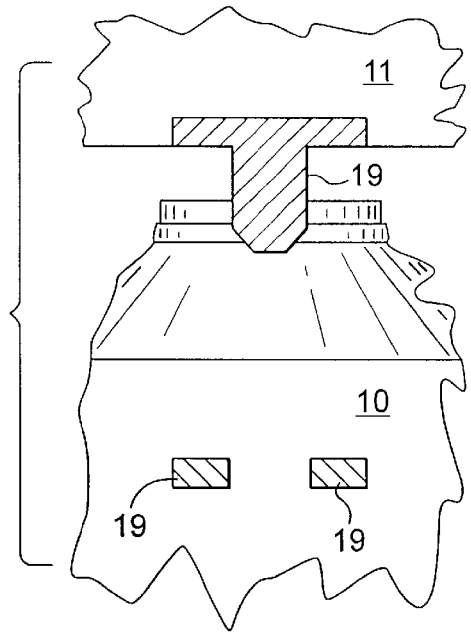
Figure 5C:
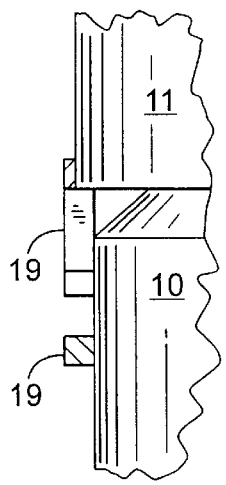
Figure 6A:
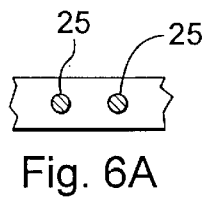
Figure 6C:
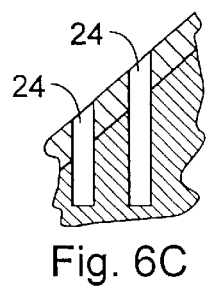
Figure 6B:
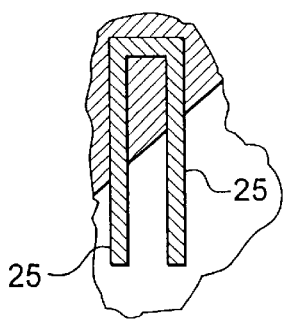
Figure 6D:
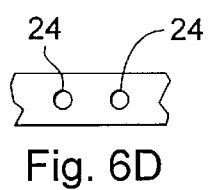

FIGS. 5A, 5B, and 5C show guide 19 as seen from above, from the right side, and in profile.

FIGS. 6A, 6B, 6C, and 6D shows surface and side views of switch 15, terminals 24, and connector 25.

OPERATION—FIGS. 1 to 6

FIGS. 1A, B, and C show the configuration of the two units that allows them to fit together. Upper unit 11 telescopes easily on to lower unit 10 to prevent access to container 12. When the units are separated, the open end of container 12 is exposed.

FIGS. 1A, B, and C show each actuator 14. In the preferred embodiment, these are electronic, slightly elevated, concave, and operable by contact. Mechanical, finger-manipulated elements are an alterative. Each set of actuators 14 is convenient for either hand. All actuators 14 on a unit must be engaged to open a latch. A breach signal 22 on each unit, seen in FIG. 1A, can be used to indicate that a hand broke engagement on actuator 14 while the units were separated.

FIGS. 2A and B show the locations of latch bolt 16 and its coupler 17 on each unit. One latch is sufficient to lock the units together because of the stable telescopic joint. To unlock the two latches, both hands must be engaged. To open bolt 16, the two units must be mated so that switch connectors 25 engage terminals 24. In the preferred embodiment, battery 21 powers motor 20 to open bolt 16. Hand-powered, mechanical means is an alternative to electronic operation to open bolt 16. If a hand disengages from any actuator 14, bolt 16 closes automatically. Mechanical, spring power can be used for this.

FIGS. 3A, 3B, 3C, and 3D illustrates the relationship of bolt 16 on one unit to coupler 17 and coupler aperture 18 on the other unit. If bolt 16 closes while the units are separated, bolt 16 will block coupler 17 and prevent assembly. A subject can not reopen bolt 16 when the units are separated. As seen better in FIG. 6, connector 25 on one unit would not bridge terminals 24 of switch 15 on the other unit. Failure of assembly indicates a breach of hand restriction. To assemble the separated units, an attendant can use a key (not shown) to complete switch the circuit.

FIG. 4A shows the slight elevation of actuator 14 and its surface concavity that facilitates engagement. The size of the contact area actuator 14, as seen from the front in FIG. 4B, balances the restriction needed to prevent cheating against the convenience needed to minimize innocent breeches of contact. The diametrically opposite thumb and finger positions are suitable for either hand.

FIGS. 5A, 5B, and 5C shows guide 19. Its projecting, upper part fits in the lower, docking parts to align the units during assembly. Proper alignment is required for coupler 17 to pass through coupler port 27 and position aperture 18 opposite bolt 16. Shelving 23 limits the telescoping of the units, as does guide 19. Stops are an alternative.

FIGS. 6A, 6B, 6C, and 6D shows the fit of connector 25 on one unit for terminals 24 on the other unit. This completes the circuit (not shown) to withdraw a detent (not shown) from bolt 16 and allow it to open. Alternatively, a mechanical switch could be used to allow bolt 16 to open. A single-action latch would be a third alternative to prevent the subject from opening bolt 16 if it is allowed to close while the units are separated.

An attendant prepares the device for each use. If the double handhold is already assembled, the attendant unlocks service door 26, removes any previous specimen, and inserts a fresh disposable element 13 and container 12. If the device is not assembled, a key (not shown) is used to complete the switch circuit. The attendant then grasps the units, engaging actuators 14 to open latch bolts 16 and assemble the double handhold. The key is removed, and the container is secure. The subject is instructed to keep both hands continuously engaged on the actuators to separate the units, expose the container to void, and reassemble the device. A lavatory or other area is used for privacy to void the specimen. If hand restriction is not maintained until the two units have been reassembled, bolt 16 closes, and the units do not fit together. Thus, any breach of hand restriction would be evident when the attendant returns.

In the preferred embodiment, container 12 rests in disposable element 13 in the lumen of lower unit 10, as in FIG. 2A. This protects container 12 from direct contact with the apparatus and possible contamination. Inexpensive plastic cups are sufficient for this purpose. A simple stand may be used to support the device to prevent spilling the specimen after the double handhold has been reassembled.

The device can be made with a smaller diameter by rotating the latching mechanism 90°. Bolt 16 would then move parallel, rather than perpendicularly, to its unit's wall. Rotation could be used also to increase the diameter of the lumen for container 12.

The latching mechanism could be incorporated into the guide or by adding a similar surface structure A latch bolt in one part would enter a chamber in the other part. Two independent latch sets would be needed. These could be housed in the same or separate structures. An exposed coupler would be unnecessary. The external dimensions of the device would be similar to the preferred embodiment. The interior and the latch mechanism would be less easily soiled. A disadvantage would be the bolt end's exposure. A subject might contrive to block the bolt from automatically projecting if hand-restriction should be breached. In the preferred embodiment, the bolt is not exposed, and tampering damage to the coupler would be obvious. With the preferred embodiment, soiling is more likely but is easily cleaned through the service doors.

Breach of hand restriction could be detected without a switch. A counter could record the number of times a latch is opened or an actuator is engaged. Another alternative would be transmission of an audio or visual signal each time such action occurs.

The mechanisms and structures of the double handhold are simple. Plastic, fiberglass, and metal alloys are sufficiently impervious for use in the device.

The description above is meant to explain the invention and illustrate its embodiment, rather than to limit its scope. For example, the units, latches, actuators, and guides may have various shapes, mechanisms, and dispositions. It is also possible to further limit the movement of either hand, particularly for the upper unit. Collars, finger sleeves, smaller contact actuators, or additional actuators can restrict even minimal movement. These might, theoretically, be useful if a subject has a magician's skills. Many materials are suitable for constructing the device and its various parts. Other operating systems and power sources are feasible. The scope of this invention should be determined, therefore, by the claims and their equivalents.

I claim:

1. A double handhold for restricting a subject's hands from putting a false urine specimen into a container, said double handhold consisting of two units reversibly assembled together, wherein said double handhold prevents access to said container when said double handhold is assembled, and allows said access when said double handhold is not assembled; and wherein said two units comprise:
   a. a first unit having means for holding said container, and
   b. a second unit having means for preventing access to said container when said two units are assembled together; and wherein each of said first and second units comprises:
      1) configuration means for assembling one of the first or second units to the other of said first or second units, whereby said two units can be locked together;

2) latch means operable to close automatically if not held open, and said latch means operable, when closed, to
a) lock said two units together when said two units are assembled, and to
b) block assembly of said two units when said two units are separate; and
3) actuator means located on a surface of each unit which is to be engaged by a subject's hands and, operable, while engaged by one of said subject's hands, to open and to hold open said latch means; whereby said subject must engage both hands on said actuator means on both said first and second unit to separate and to assemble said two units.

2. The double handhold of claim 1 wherein said means for holding said container comprises a lumen for housing said container.

3. The double handhold of claim 1 further including switching means for permitting at least one said latch means to open, said switching means comprising a first element on one of said two units and a second element on the other one of said two units; and wherein assembly of said two units places said first element in operable position with said second element, said operable position permitting said latch means to open;

whereby said subject cannot reopen at least one said latch means and therefore cannot assemble said two units if said subject's hands do not continuously engage all of said actuator means on the two units while said two units are separated.

4. The double handhold of claim 1 and further including single-action latch means for preventing said subject from reopening said latch means after said latch means have been closed while said two units are separated from one another wherein a breach of procedure is evident.

5. The double handhold of claim 1 and further including signaling means comprising a signal and means for connecting said signal to said latch means; thereby indicating disengagement of said actuator means by said subject's hands while said two units are separated.

6. The double handhold of claim 1 and further including at least one detecting means for revealing a breach of hand restriction, said at least one detecting means including counting means and transmission means, both indicative of action of said latch means.

7. The double handhold of claim 1 wherein said actuator means comprises means for placing said subject's fingers and thumb thereon, where placing are positioned diametrically opposite to each other; whereby either one of said subject's hands can engage said actuator means on either one of said two units.

8. The double handhold of claim 1 wherein said two units have configurations for partly telescoping said two units together; whereby they can be locked together by at least a single said latch means.

9. The double handhold of claim 1 and further including guiding means for facilitating the assembly of said two units.

10. A method for restricting the hands of a subject voiding into a container, said method comprising:
a) providing a self-contained, double handhold consisting of two separate one-hand-restricting units reversibly assembled together to enclose a container; wherein said one-hand-restricting units are operable, when continuously engaged by said subject's two hands, to be separated to allow access to said container and then to be reassembled; and each unit having at least one means for indicating a breach of hand engagement on said unit, said means comprising action-signaling means, action-counting means, single-action latch means for preventing a latch from reopening, and switching means for preventing a latch from opening when said two units are separate;
b) providing a container in one of the separate units;
c) preventing access for voiding into said container until one of said subject's hands is engaged by one of said units while the other of said subject's hands is engaged by the other of said units;
d) allowing access for voiding into said container as long as each hand is engaged by a separate one of said units; and
e) preventing further access to said container when either of the subject's hands is disengaged from one of said units.

* * * * *